United States Patent [19]

Takahashi et al.

[11] Patent Number: 4,799,783

[45] Date of Patent: Jan. 24, 1989

[54] EYE FUNDUS CAMERA

[75] Inventors: Junichi Takahashi; Yuji Itoh, both of Kanagawa, Japan

[73] Assignee: Canon Kabushiki Kaisha, Tokyo, Japan

[21] Appl. No.: 65,072

[22] Filed: Jun. 18, 1987

Related U.S. Application Data

[63] Continuation of Ser. No. 842,769, Mar. 24, 1986, abandoned, which is a continuation of Ser. No. 782,180, Sep. 30, 1985, abandoned, which is a continuation of Ser. No. 668,700, Nov. 6, 1984, abandoned, which is a continuation of Ser. No. 352,761, Feb. 26, 1982, abandoned.

[30] Foreign Application Priority Data

Mar. 9, 1981 [JP] Japan .................................. 56-33562
Mar. 31, 1981 [JP] Japan .................................. 56-47616

[51] Int. Cl.$^4$ ............................................. A61B 3/14
[52] U.S. Cl. ................................................. 351/206
[58] Field of Search ............... 350/206, 207, 208, 209, 350/211, 212, 221

[56] References Cited

U.S. PATENT DOCUMENTS 3,851,954 12/1974 Kato et al. .................... 351/207
4,146,310 3/1979 Kohayakawa et al. ........... 351/207

OTHER PUBLICATIONS

Matsui, Simultaneous Stereophotogrammetric and Angiographic Fundus Camera, 1978 Am. Journal of Opht. vol. 85.

Degenhardt, The New Zeiss Retinal Camera, 1956 British Journal of Photography.

Primary Examiner—Rodney B. Bovernick
Assistant Examiner—P. M. Dzierzynski
Attorney, Agent, or Firm—Toren, McGeady & Associates

[57] ABSTRACT

An eye fundus camera including a photographic system for photographing the fundus of an eye and forming an imaging optical path having an illuminating system for illuminating the eye fundus and forming an illuminating light path, a barrier filter releasably seated in the imaging optical path, and an exciter releasably seated in the illuminating optical path. The apparatus also includes a diaphragm arranged in the illuminating optical path for changing the illuminated field on the eye fundus, an optical device in the imaging optical path for changing the magnification of the photographic system, or an apertured plate in the same path to change the photographic field, and a drive connection device responsive to insertion of the barrier filter and exciter into the path for enlarging the diaphragm and for reducing the magnification of the photographic system, or increasing the size of the opening in the apertured plate.

34 Claims, 15 Drawing Sheets

F I G.12
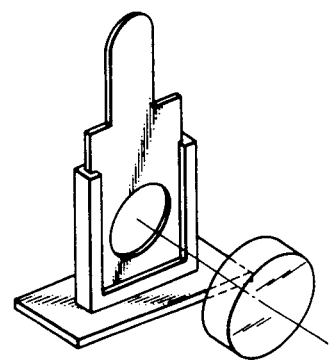
F I G.13
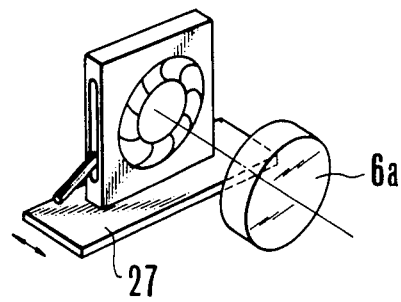

EYE FUNDUS CAMERA

This is a continuation of application Ser. No. 842,769, filed Mar. 24, 1986, which in turn is a continuation of application Ser. No. 782,180, filed Sept. 30, 1985, which in turn is a continuation application of Ser. No. 668,700, filed Nov. 6, 1984, which in turn is a continuation application Ser. No. 352,761, filed Feb. 26, 1982 all of which are now abandoned.

BACKGROUND OF THE INVENTION

1. Field of the Invention

This invention relates to eye fundus cameras capable of selectively performing fluorescein angiography of the fundus of an eye and the color or monochromatic photography (called normal photography).

2. Description of the Prior Art

The angular fields of the non-contact type eye fundus cameras have for a long time conventionally been in the order of 30 degrees. Recently, however, as the design of wide angle objective lenses has advanced and the method of removing the disturbing reflections and scattering the illuminating light bundle has advanced, the angular field has exceeded 45 degrees. Since the use of the wide angle objective lens makes it possible to take photographs of a large area of the eye fundus in a reduced number of shots with a reduction in the required number of photographs for every specimen, it becomes easier to make photographs of almost equal image quality. The patient will have less pain and there is a great demand for increasing further the wide angular field.

One of the important factors for increasing the field angle is to eliminate the disturbing light. Since the photographic system and the illuminating system are coaxially arranged in the eye fundus camera, it has been a long established practice in the art that, in order to prevent a portion of the illuminating light reflected on the cornea to migrate into the photographic system, a control obscuring diaphragm is provided in the illuminating light path, thus shutting out the light which would otherwise impinge on the cornea. Since the objective lens has an angular field of 45° or more, however, the presence of undesirable reflections on the crystalline lens poses a serious problem. In the conventional narrow angle eye fundus camera (30°), the image of the shade of the obscuring diaphragm overlaps not only the reflective area of the cornea but also the crystalline lens. But the increase in the angular field of the objective lens calls for a decrease in the size of the shade of the obscuring diaphragm so that even the crystalline lens forms a source of undesirable light.

As the counter-measure for this, Japanese Patent Sho No. 51-24249 (U.S. Pat. No. 3,851,954) discloses that at the front surface, or at an intermediate point between the front and rear surfaces of the crystalline lens, there is formed a baffle image to eliminate the reflections on the crystalline lens. Japanese Laid Open Utility Model Sho No. 52-107140 (U.S. Pat. No. 4,102,563) discloses that the illuminating system is provided with a black point conjugate to the rear surface of the crystalline lens eliminating the scattering light within the crystalline lens and from the rear surface thereof.

Aside from this, in eye fundus cameras, a limitation is that the fundus of an eye to be examined is illuminated by a light bundle passing through the pupil thereof. The higher the level of illumination, the more desirable it is. It is, therefore, preferable to increase the diameter of the pupil. As the age of the patient increases, however, a sufficient dilation of the eye's pupil becomes more difficult even if a mydriatic is applied to the eye. Therefore, the selectable pupil diameter in actual practice must be considerably smaller than the maximum possible one. In the undesirable light eliminating method, as the angular field widens, the area which must be shielded from light increases, thereby giving rise to the problem that within the framework of the limited pupil diameter, total elimination of undesirable light becomes difficult. Accordingly, it is much desired to compromise the requirements of preserving the high image quality and of increasing the angular field, or decreasing the pupil diameter.

On the other hand, the ordinary eye fundus cameras, besides being capable of normal photography, are adaptable to fluorescein eye fundus angiography. Fluorescein angiography of the eye fundus is such that when the fluorescein sodium injected from an elbowvein reaches the blood circulation system in the eye, the ocular fundus is illuminated by an excited light of wavelengths of a nearly blue color so that as the blood columns are caused to give off fluorescein light, suitable photographic film is exposed to remove only the fluorescein light from the light rays returning from the eye to be examined. For this purpose, use is made of a barrier filter in the photographic ray path of light, and of an exciter in the illuminating ray path of light to separate the wavelengths.

The present inventors have, in the preceding Japanese Laid Open Patent Sho No. 55-26959, considered that when in fluorescein angiography the illuminating light and the photographing light are differentiated in wavelength from each other, a proposal is made that the baffle for removing the disturbing light has to be demounted with the advantage that the illumination level is increased. Since, as a result of the wavelength separation, the rays of light which have wavelengths in the illuminating wavelength region are blocked by the barrier filter, it doesn't matter if a disturbing light is produced provided that it has a wavelength in the region, since this does not lead to badly deteriorate the image quality. Another arrangement for eliminating the function of the baffle is also disclosed in U.S. patent application Ser. No. 32,683.

SUMMARY OF THE INVENTION

It is an object of the present invention to provide a fundus camera capable of selectively performing normal photography and fluorescein angiography wherein the angular field in fluorescein angiography is wider than that in normal photography.

Another object is to provide normal photographs with excellent image quality.

Still another object is to heighten the magnification in normal photography more than that in fluorescein angiography.

It is to be noted that when increasing the angular field of the objective lens, for example, an invention in Japanese Laid Open Patent Sho No. 52-141094 (U.S. Pat. No. 4,176,920) has already solved the appendant problems and, therefore, it is possible to design a photographic system having an increased angular field and an illuminating system having an increased angle of projection.

BRIEF DESCRIPTION OF THE DRAWINGS

FIGS. 11, 12 and 13 are perspective views of movable illumination field stops;

DESCRIPTION OF THE PREFERRED EMBODIMENTS

Figure 1:
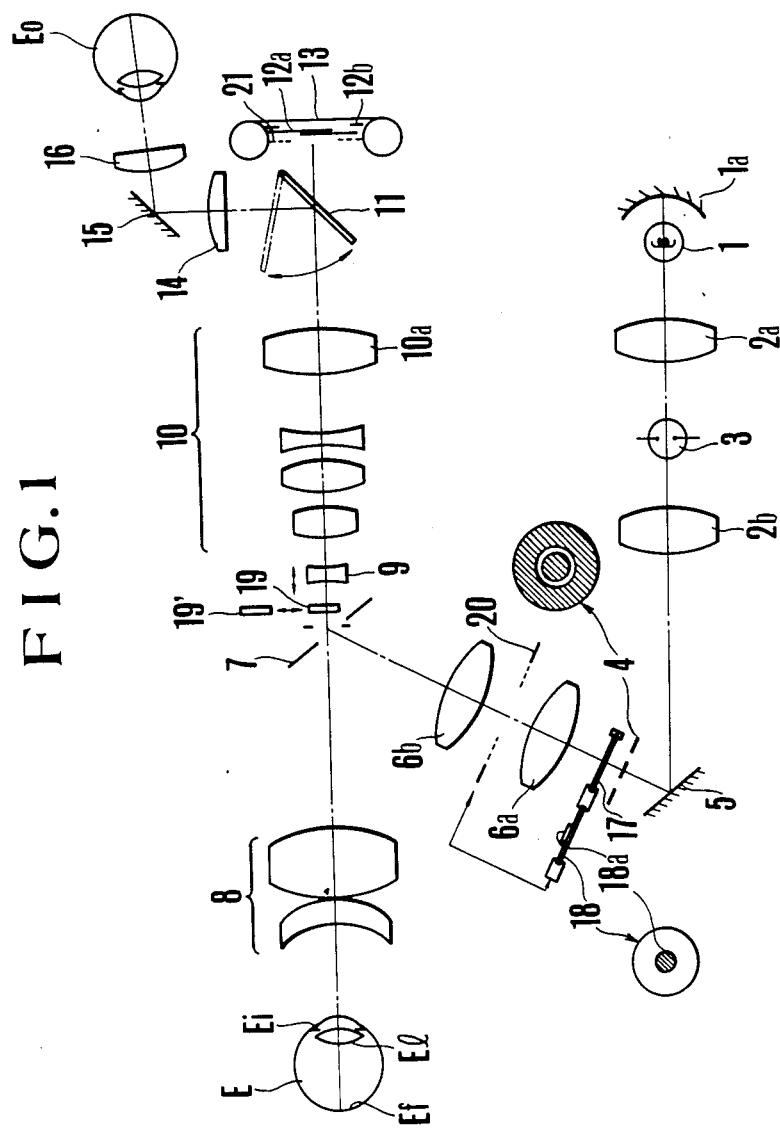
FIG. 1 is a sectional view of an embodiment of an eye fundus camera, according to the present invention.

In FIG. 1, there is shown an eye E to be examined; its tris Ei; the crystalline lens El and the ocular fundus Ef.

Also, there is shown an observation light source 1 such as a tungsten lamp; a reflector 1a; condenser lenses 2a and 2b; a photographic light source 3 such as a xenon discharge tube; a ring slit plate 4 has an annular opening; and a mirror 5.

The apparatus also includes relay lenses 6a and 6b; a beam splitter 7a such as a mirror having an opening at the center thereof; and an objective lens 8 provided with a front aplanatic lens for the purpose of increasing the angular field. Also included is a focusing lens 9; a photographic lens group 10; a movable mirror 11; a shutter 12a; a photographic field stop 12b; a film 13; a field lens 14; a mirror 15; an eyepiece 16; and the eye of an observer is Eo.

This eye fundus camera has functions outlined below. The light sources 1 and 3 are conjugate to each other. The light source 3 is conjugate with respect to the condenser lens 2a. The other condenser lens 2b forms an image of the light source near the ring slit plate 4, and then the relay lenses 6a and 6b form an image of the annular opening 4 near the beam splitter 7. Its mirror action shifts it to the left. The objective lens 8 forms a second image of the annular opening 4 near the iris Ei, thus finally illuminating the eye fundus Ef. The foregoing parts constitute an illuminating ray path of light. When observing, the light source 1 is turned on, while when photographing, the second light source 3 is turned on instead.

Further description is given to an image forming system. The reflected light from the eye fundus Ef goes to the right. After having once been focused by the crystalline lens El and the objective lens 8, it passes through the beam splitter 7 and a photographic stop (not shown) to form a sharp image by the focusing lens 9 and the photographic lens group 10. When in observation, however, it is directed upwards by the movable mirror 11 in the position illustrated by the solid lines to form an equivalent image which is observed through the finder (14–16). When photographing, the movable mirror 11 is flipped upwards to the position illustrated by the dot and dash lines, and then the shutter is opened to expose the film 13.

The member 17 between the mirror 5 and the relay lens 6, is an exciter filter which is inserted into the illuminating ray path of light when in fluorescein angiography and which is taken out of the path when in normal photography. After the exciter filter has been removed, a baffle 18a equipped light permeable plate 18 is placed instead by a mechanism to be described below, and that the lengths of the optical paths of the filter and the transparent plate are equal to each other. The baffle 18a is arranged on the optical axis and at a conjugate position to the fundus side surface of the crystalline lens El, and has a function of removing the disturbing reflections on the crystalline lens. Instead of forming an image of the baffle in the crystalline lens, it is possible to obscure the same illuminating light bundle by forming an aperture opening just in front of the cornea. In the latter case, this baffle must be replaced by an apertured plate. Where conservation of the illumination level need not be considered, the baffle may be fixedly mounted, while the exciter filter is releasably mounted at another position.

Furthermore, a barrier filter 19 is releasably mounted in the light path moving either independently of, or in connection with, the filter 17. An illumination field stop is identified by the numeral 20. The illumination field stop 20 is at a conjugate position to the fundus of the normal eye (the eye of zero diopter). In normal photography, the illumination field stop 20 is inserted into the illumination ray path of light when detaching the exciter filter 17 from the optical path, thereby the light bundle is stopped down. The resultant reduction in size of the stop opening corresponds to the magnitude of the marginal zone which is not to be photographed when the angular field takes a presumed value for normal photography,. Therefore, this marginal zone is obscured by the shadow (image) of the stop. In more detail, since determination of the angular field for normal photography accounts for the disturbing reflection eliminating mechanism, as the angular field for fluorescence is wider than that for normal photography, and the projection angle of the illuminating light is coincidental with the field angle for fluorescein angiography, it follows that with the eye fundus camera having a constant angle of illumination projection, the fundus of the eye is illuminated over a greater range than in normal photography. As the present inventor has pointed out in Japanese Laid Open Patent Sho No. 54-141095 (U.S. patent application Ser. No. 32,683), those of the illuminating rays of light which are beyond the photographing area of the eye fundus, when scatteringly reflected from the outside area of the eye fundus, greatly contribute to a flare as they migrate into the photographing rays of light. Therefore, it is desirable to eliminate this unnecessary illuminating light.

The member 21, just in front of the shutter 12, is a baffle having an aperture opening and which defines the range of a photographic field for normal photography as stopped down from the photographic field stop 12b for fluorescein angiography. This baffle 21 is inserted into a position illustrated by dotted lines when detaching the filter for fluorescein angiography. Since, however, this position is very near the film 13, it is substantially conjugate to the eye fundus Ef. It is also noted that the photographic field defined by the aperture opening of the baffle 21, though being narrowed, is the same as that of the conventional angular photography field prior to the present invention. (It is of course possible to extend the photographic field). It is also noted that if the focusing adjustment automatically accurately adjusts a given visibility of the eye to be examined and the illumination field stop 20, insertion of the baffle 21 is omitted.

With this type of camera, when in normal photography, instead of the exciter filter 17 being inserted, the baffle 18a is inserted into and seated in the optical axis, and the illumination field stop 20 is either inserted or closed down. Furthermore, instead of the barrier filter 19, a transparent compensation plate 19' of the same optical path length is inserted. Then, after the photographic field stop 21 has been mounted, observation followed by exposure is carried out in a similar manner to that in the prior art. Otherwise in fluorescein angiography, the baffle 18a is replaced by the exciter filter 17, and the photographic field stops 20 and 21 are either removed or fully opened. Then the barrier filter 19 is further inserted. The illumination system has an increased angle of projection, and the photographic system has an increased angular field so that fluorescein angiography of a far wider angular field than that of normal photographs can be obtained. Practical examples of mechanisms for attaching andd detaching the filter for fluorescein angiography, for mounting and demounting the field stop, and for closing down the stop are described below in greater detail. The accompanying drawings depict the essential parts thereof.

Figure 2:
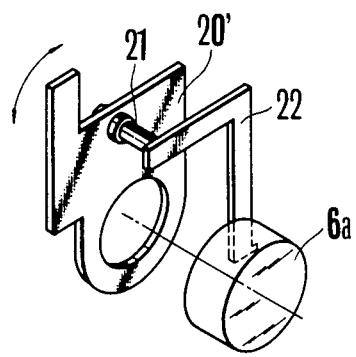
FIGS. 2, 3 and 4 are perspective views of illumination field stops respectively.
Figure 3:
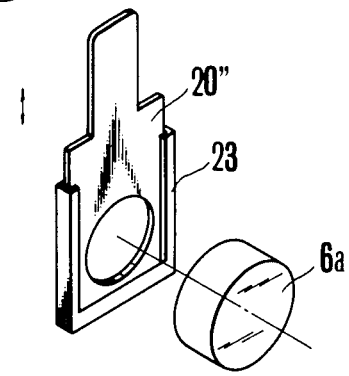
Figure 4:
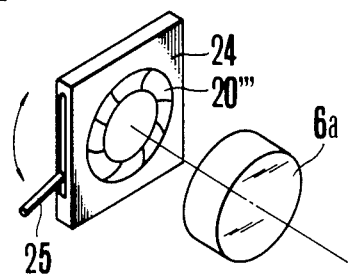

FIG. 2 illustrates the illumination field stop in the form of a pivotal plate 20' rotatably mounted on a shaft 21 which is the center of rotation, which is fixedly mounted on a support 22, and enters into and retracts from the optical path, while being restrained from axial movement. FIG. 3 illustrates another method of inserting and retracting the illumination field stop plate 20" into and from the optical path as it linearly moves along a guide plate 23. FIG. 4 illustrates the illumination field stop in the form of an iris diaphragm 20''' provided with blades in a guide plate 24 and being opened and closed by a control pin 25.

When switching the camera between the modes of fluorescein angiography and normal photography, change of the illumination field stop may be effected in isolation from the attachment and detachment of the filter for fluorescein. Since the changeover between fluorescein angiography and normal photography is always associated with mounting and dismounting the filter for fluorescein angiography, a simple and reliable way to operate the illumination field stop along with the fluorescein filter is by drive connections illustrated in FIGS. 5 to 7.

Figure 5A:
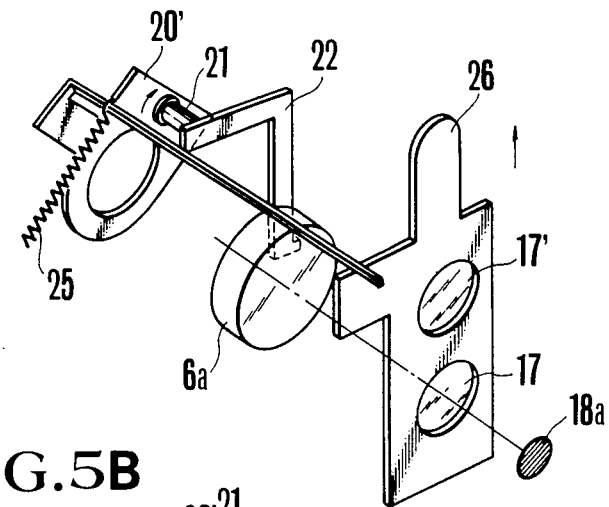
FIGS. 5A and 5B, 6A and 6B, and 7A and 7B are perspective views of drive connection mechanisms of the illumination field stops with respective fluorescence.

FIG. 5A illustrates an operative position for fluorescein angiography. When a fluorescein filter frame 26 is lifted upwards, as viewed in the drawing, the exciter filter 17 enters the optical path. An optical path length compensation glass 17' is equivalent to the exciter filter. The baffle 18, for removal of the undesirable light, is assumed to be operable independently of the optical path length compensation glass. It is also noted that if the exciter filter is as thin as a gelatin filter, there is no need to use the optical path length compensation 17'. At this time, the photographic optical path contains the barrier filter 19. As is well known, the exciter filter and the barrier filter have different permeable wavelength regions from each other so that even when the rays of light transmitting through the exciter filter produce scattering reflections on the marginal zone of the fundus of the eye, the image quality is not affected.

Figure 5B:
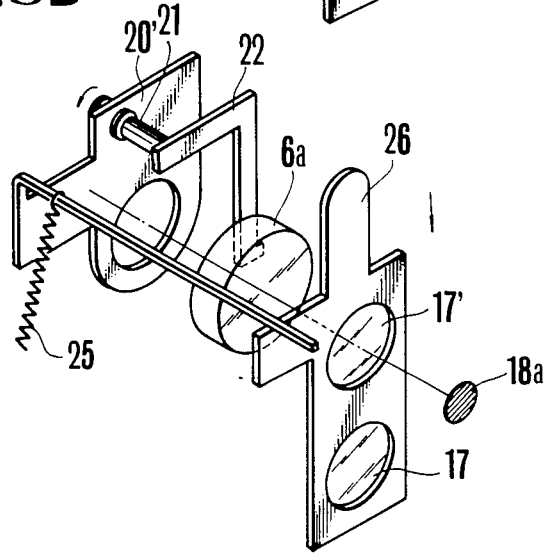

FIG. 5B illustrates another operative position for normal photography. When the fluorescein filter frame 26 is pushed down as illustrated, the illumination field stop 20' turns about the shaft 21 under the action of a spring 25, thus being mounted in the optical path. In normal photography, the scattering of undesirable reflections on the marginal zone of the fundus, which would otherwise lower the image quality, can be eliminated.

Figure 6A:
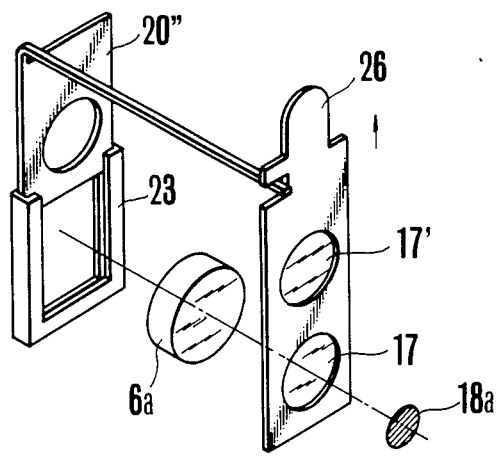
Figure 6B:
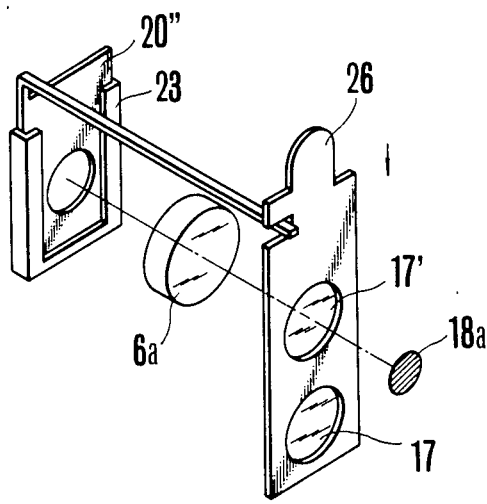
Figure 7A:
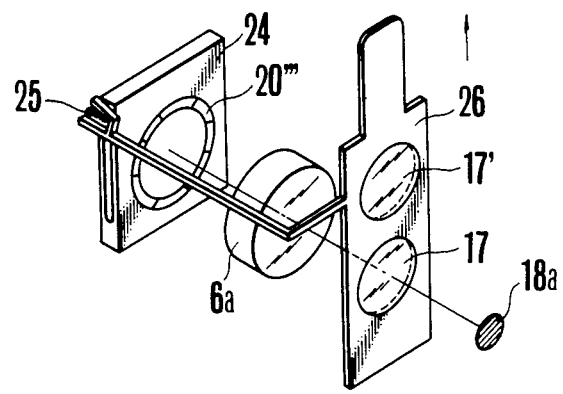
Figure 7B:
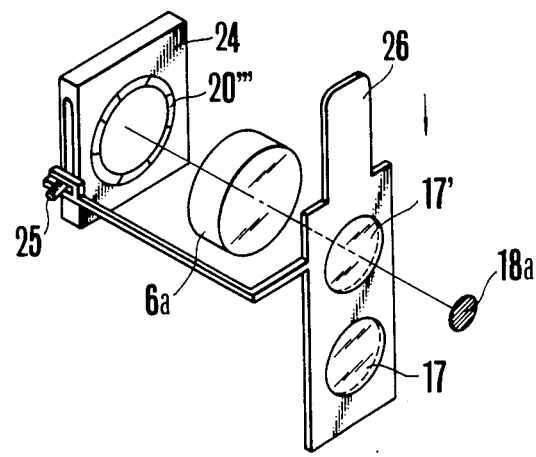

The same is true with FIGS. 6 and 7. FIG. 6A illustrates that when fluorescein angiography is under operation, when the illumination field stop 20" escapes from the optical path, it is moved along the guide plate 23 by the fluorescein filter frame 26. FIG. 6B illustrates normal photography showing that the illumination field stop 20' is in the optical path as it has been moved along the guide 23 by the fluorescein filter frame 26. FIG. 7A also illustrates that when fluorescein angiography is under operation, the stop control pin 25 has been moved by the fluorescein filter frame 26 so that the diaphragm blades defining the illumination field stop 20''' are in a fully open position. FIG. 7B represents normal photography with the stop control pin 25 closing down the illumination field stop in connection with the fluorescein filter.

As has been described above, the small size baffle 18a, illustrated in FIGS. 5, 6 and 7, is conjugate to the fundus side surface of the crystalline lens El so that the illuminating light is partly shut out forming a shade on the fundus side surface of the crystalline lens, thus eliminating the disturbing reflections on the crystalline lens. This is necessary to normal photography. In fluorescein angiography, however, it is no longer necessary because of the isolation of a wavelength region by the barrier filter and the exciter filter. For this reason, the baffle 18a is permitted to lie in the optical path when involved in normal photography, and to escape from the optical path when involved in fluorescein angiography. FIG. 8 depicts this.

Figure 8A:
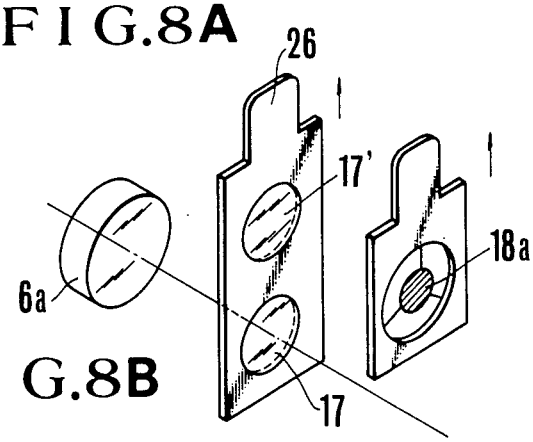
FIGS. 8A and 8B are perspective views of a drive connection mechanism of the fluorescence filter and a baffle for removal of disturbing light.
Figure 8B:
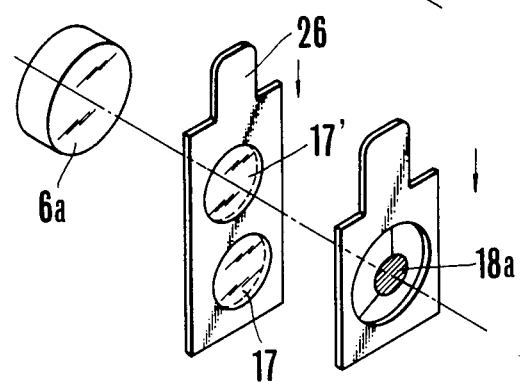
Figure 9:
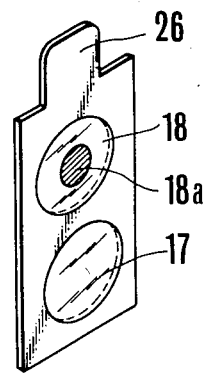
FIG. 9 is a perspective view of a filter frame.

In FIG. 8A, the exciter filter 17 lies in the optical path, while the baffle plate 18a has escaped therefrom. In FIG. 8B, while the exciter filter 17 has escaped from the optical path, the baffle plate 18a is therein. If the scheme of FIG. 8 operates with the fluorescein filte, the control is quick, easy and reliable. FIG. 9 illustrates a form of operative connection with the fluorescein filter.

It is to be understood from FIG. 9 that it is mounted in fixedly secured relation to the fluorescein filter carrier at the optical path length compensation glass equivalent to the fluorescein filter.

Figure 10:
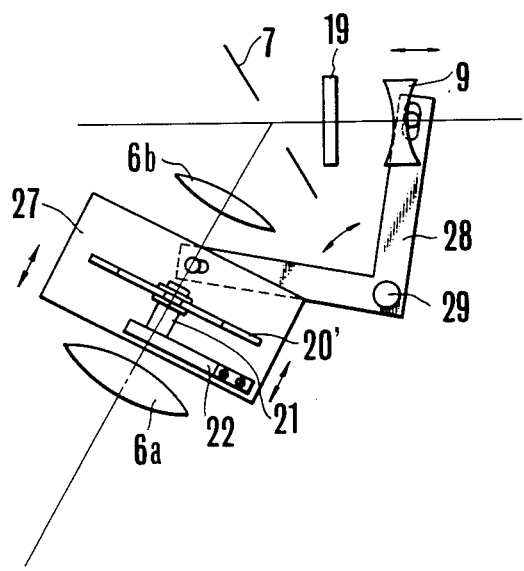
FIG. 10 is a perspective view of a mechanism for displacing the focusing stop.
Figure 11:
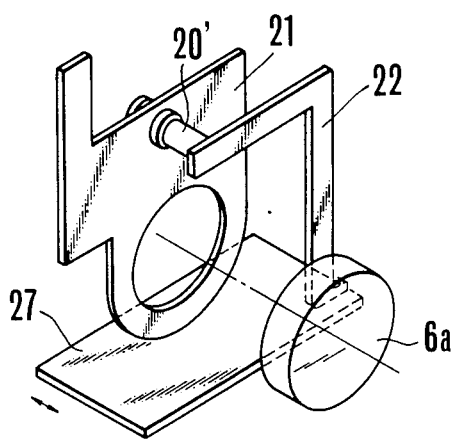

The illumination field stops which so far have had a maximum effect, provided that they always take a conjugate position to the eye fundus Ef rgardless of the visibility of the eye to be examined. Because of this, the position of the illumination field stop must be adjusted in accordance with the position of the focusing lens 9. FIGS. 10 and 11 illustrate a mechanism for operative connection between the focusing lens and the illumination field stop. A focus shaft 29 is fixed to a focus knob (not shown). A focus lever 28, on one hand, is fixed to the focus shaft 29, and, on the other hand, is connected to the focus lens 9 by a pin and a slot, so that the focus lens 9 is axially moved by the focusing operation. A movable plate 27 moves in an axial direction with respect to the illuminating system as guided by a guide mechanism (not shown), and cooperative with the focus lever 28 by a pin-and slot connection. The illumination field stop 20' is mounted on the shaft 21 formed as a unit with the shaft support 22, which is fixed to the moving plate 27 in such a manner that it can turn about the shaft 21, but cannot move axially. Therefore, when focusing is performed, as the focusing lens 9 moves to effect coincidence of the focal point of the photographic system with the eye fundus, the illumination field stop 20' takes the conjugate position to the eye fundus Ef. FIGS. 12 and 13 illustrate forms of fixing the different illumination field stops to the moving plate 27.

Figure 14:
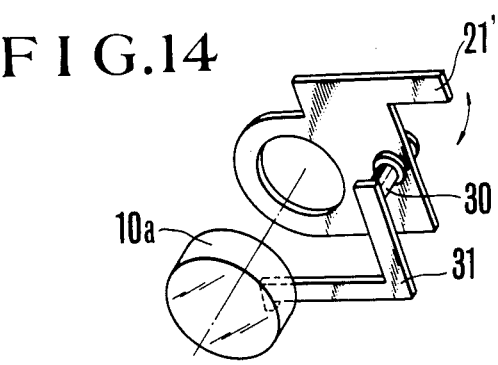
FIGS. 14, 15 and 16 are perspective views of photographic field stops.
Figure 15:
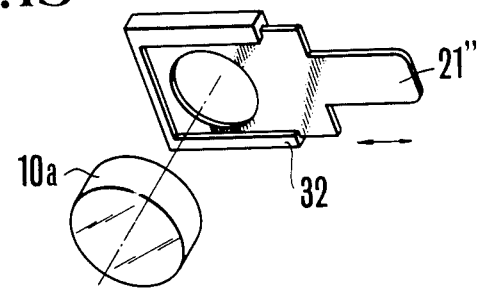
Figure 16:
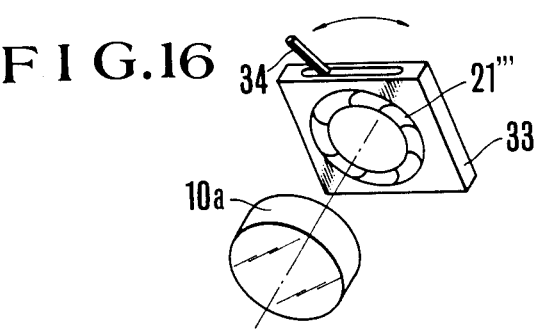

The stop form may be a baffle plate as illustrated in FIGS. 14 and 15 at 21' and 21", or an iris diaphragm of variable opening size as illustrated in FIG. 16.

When in fluorescein angiography and in normal photography, as the means of alternating the photographic field stop, there are methods illustrated in FIGS. 14, 15 and 16. In FIG. 14, the photographic field stop 21' enters into and escapes from the optical path as it turns about a shaft 30 fixed to the shaft support 31. In FIG. 15, the photographic field stop 21" linearly moves along a guide plate 32 into and away from the optical path. In FIG. 16, the photographic field stop 21'" is defined by diaphragm blades, which are operated to open and close within the diaphragm blade guide plate 33, by a control pin 34. When switching the camera between the fluorescein exposure mode and the normal exposure mode, the change of the photograhic field stop may be independently carried out of the attachment and detachment of the fluorescein filter. Since, however, the changing over of fluorescein angiography and normal photography is always associated with the attachment and detachment of the fluorescein filter, it is easy and reliable to use an operative connection with the fluorescein filter, as illustrated in FIGS. 17 to 19.

Figure 17A:
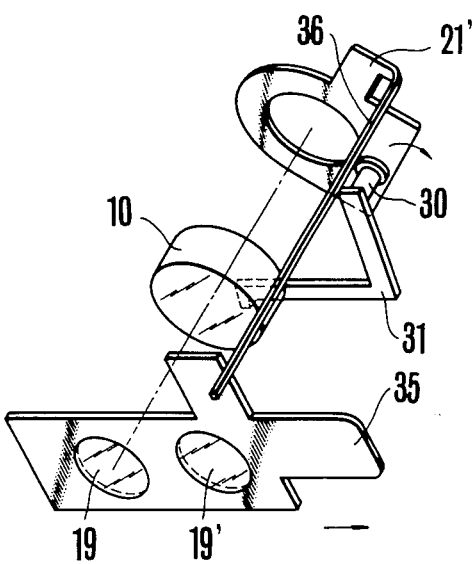
FIGS. 17A and 17B, 18A and 18B, and 19A and 19B are perspective views of drive connection mechanisms of the photographic field stops and of the filters for fluorescein angiography.
Figure 17B:
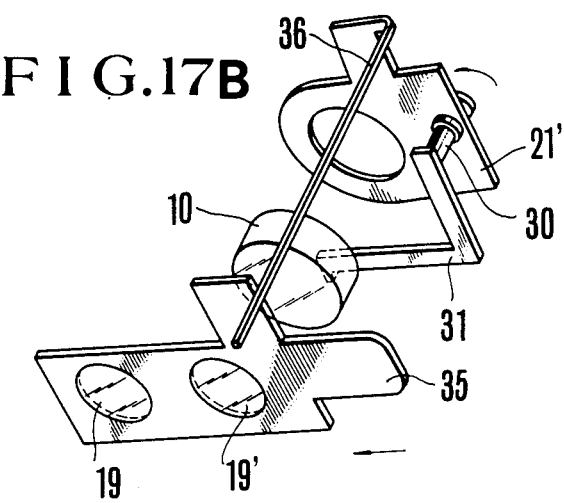

FIG. 17 illustrates an operative position for fluorescein angiography. When a fluorescein filter frame 35 is pulled upwards, a barrier filter 19 enters the optical path. An optical path length compensation glass 19' is equivalent to the barrier filter 19. If the barrier filter 19 is as thin as a gelatin filter, the optical path length compensation guide 19' is no longer necessary. At this time, an exciter filter 17 is inserted into the illumination optical path.

FIG. 17A illustrates another operative position for normal photography. When the fluorescein filter frame 35 is pushed down, as illustrated in the drawing, the photographic field stop plate 21' is turned about the shaft 30 and into the optical path by the spring 36. Thereby, it is possible to stop the undesirable scattering of light from the marginal zone of the eye fundus, which would otherwise cause a loss in image quality in normal photography.

Figure 18A:
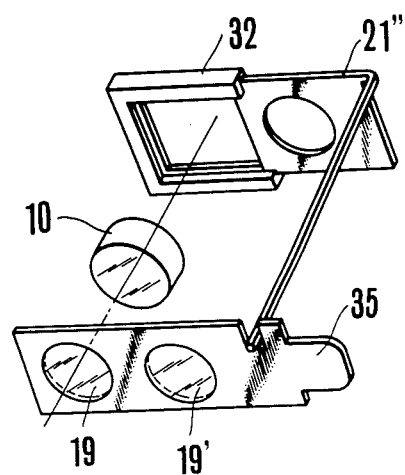
Figure 18B:
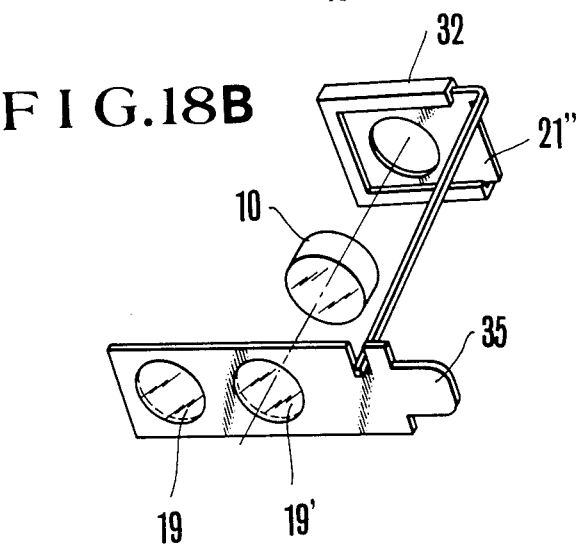
Figure 19A:
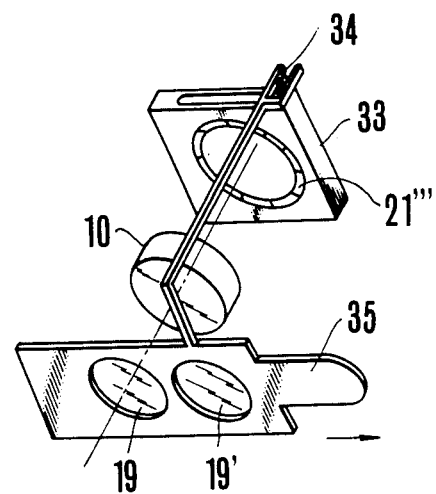
Figure 19B:
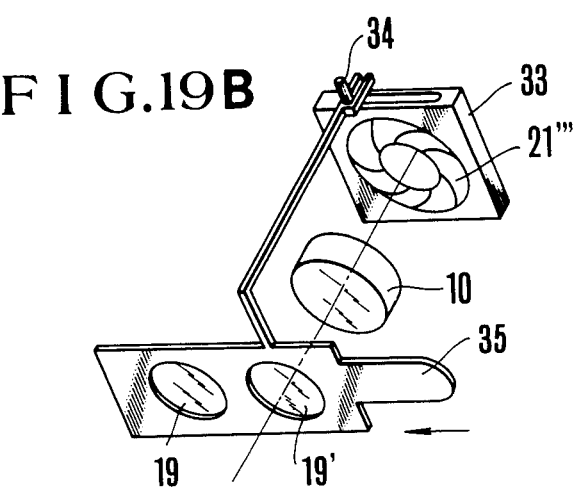

FIG. 18A illustrates an event when fluorescein angiography is operating with the photographic field stop 21" disposed out of the optical path after having been moved along the guide plate 32. FIG. 18B illustrates an even when normal photography is under operation, showing that the photographic field stop 21" after it has been moved into the optical path by movement along the guide 32 of the fluorescein filter frame. FIG. 19A illustrates an event when fluorescein angiography is under operation with the photographic field stop 21'", of an iris form, disposed in the fully open position after the diaphragm control pin 34 has been operated by the fluorescein filter frame. FIG. 19B illustrates another event when normal photography is under operation, showing that the photographic field stop has been closed down by the control pin 34 cooperating with the fluorescein filter.

Another method of alternating the photographic field stop is by using an exposure aperture. At the present time, in fluorescein angiography and normal photography, a number of color photographs followed by fluorescein angiography are taken for every patient. Because different types of film are used, the film camera body must be interchanged.

Figure 20A:
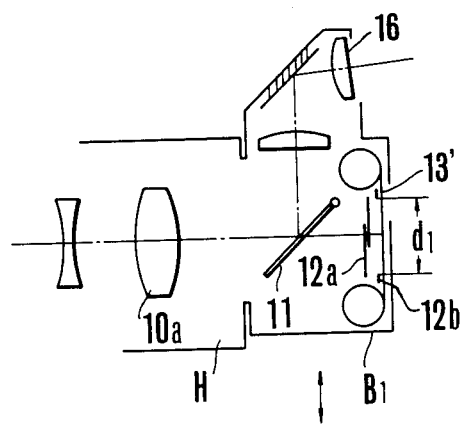
FIGS. 20A and 20B are fragmentary sectional views illustrating interchange of the film camera body.
Figure 20B:
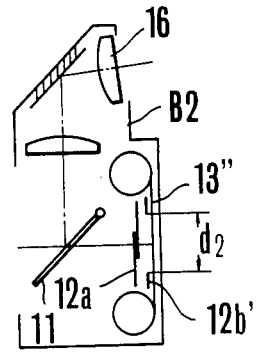

Alternation of the photographic field stop may be otherwise effected by selectively using film camera bodies of different size apertures for fluorescein angiography and normal photography. FIGS. 20A and 10B illustrate the main part of the body of the eye fundus camera at H, with an interchangeable film camera body B1 for fluorescein angiography and another interchangeable film camera body B2 for normal photography, both being selectively attached to the main part H of the camera body. The bodies B1 and B2 are different from each other not only in that the used films 13' and 13" are of different types, but also in that the aperture size d1 of the fluorescein angiographic field stop 12b is different from the aperture size d2 of the normal photographic field stop 12b'. As a result, when the film camera body B1 for fluoresceiin angiography is attached, the maximum acceptable range of the photographic field for the photographic system can be photographed. When the film camera body B2 for normal photography is attached, a narrower range can be photographed. It is to be noted that when the method of interchangeably using the special camera bodies is used, it is preferable to provide for the bodies with respective signal pins controlling the attachment and detachment, or the opening and closing operation, of the illumination field stop.

Figure 21:
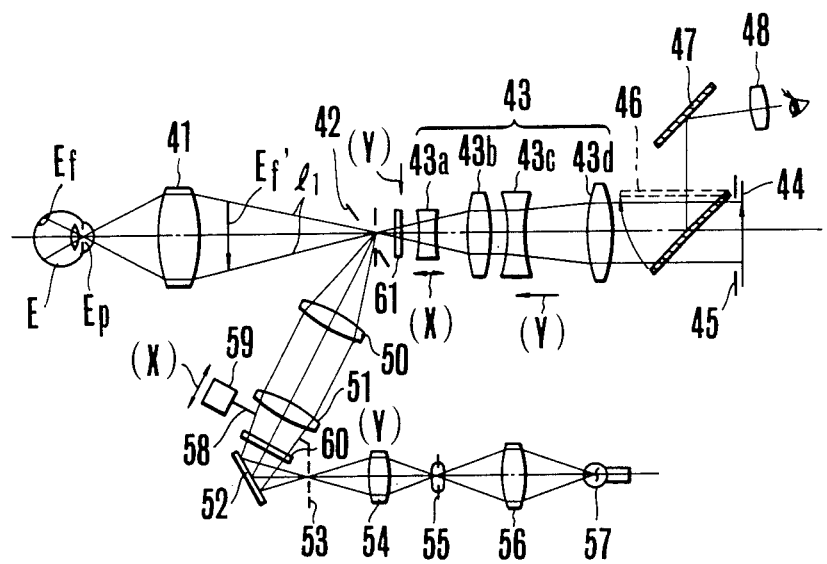
FIGS. 21 and 22 are sectional views of another embodiment of the invention.
Figure 22:
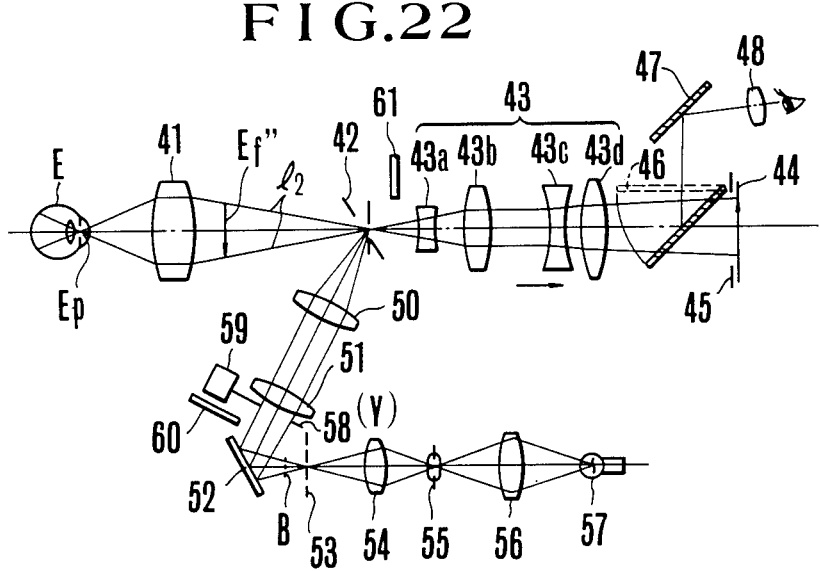

A second embodiment of the invention is shown in FIG. 21 which illustrates a case where, for fluorescein angiography, the lateral magnification is small (wide angle), and FIG. 22 which illustrates a case where, for normal photography, the lateral magnification is large (narrow angle). In these figures, an eye to be examined is identified as E and the fundus of the eye E as Ef. Elements of the apparatus include an objective lens 41; an apertured mirror 42; an image forming lens 43; and a photographic film 44. The objective lens 41, image forming lens 43, photographic film 44 and a photographic field stop constitute a photographic system with the objective lens 41 having the function of forming an image Ef' of the eye fundus, and the image-forming lens 43 refocusing that image Ef' on the film 44. A photographic field stop plate is ientified by the reference numeral 45.

It is noted that the image forming lens in this example of the embodiment includes a focusing lens 43, a positive front stationary lens 43b, a negative variator lens 43c axially movable for varying the image magnification (focal length), and a stationary relay lens 43d. It is further noted that this variator lens 43c contributes to the formation of a sharp image at only two stations in the range of movement thereof. Otherwise, a compensator may be added to effect sharp focusing over the entire range of movement thereof.

Furthermore, a quick return mirror 46 is included to the optical axis, and upon exposure retracts from the optical path. A mirror 47 changes the direction of the optical path. The mirror 47 together with an eyepiece 48 constitutes a finder system.

The apparatus also includes relay lenses 50 and 51; a mirror 52 for changing the direction of the optical path; a ring slit 53; a condenser lens 54; a light source 55 for photography such as a xenon discharge tube; another condenser lens 56; and a light source 57 for observation such as a halogen lamp. Here, the parts 50 to 57, the objective lens 41 and the apertured mirror 42 constitute an illumination system and are arranged so that the light bundles from the two light sources are collected on the ring slit 53 by the action of the condenser lenses 54, 56. The ring slit 53 is conjugate to the mirror surface of the mirror 52 with respect to the relay lenses 50 and 51, apertured mirror 42 and the objective lens 41 and, on the other hand, a light ring is formed on the pupil plane as an image of the slit portion of the ring slit 53, and this light ring expands to illuminate the eye fundus. $l_1$ identifies a principal ray of light when in the wide angle position, and $l_2$ identifies a principal ray of light when in the narrow angle position.

On the other hand, an illumination field stop 58 has the function of closing down the fundus illuminating light bundle and is conjugate to the eye fundus Ef so that the periphery of the illuminated zone of the eye fundus is obscured. It is noted that the photographic field on the eye fundus, which occurs when the variator lens 43c in the image forming lens system 43 is moved to the long focal length position to coincide with the illumination field which occurs when the stop 58 is closed down. An advantage is that the part of the light bundle which would otherwise illuminate the eye fundus beyond the photographic field does not lead to the production of scattering reflections which migrate into the photographic light bundle and, therefore, flare. This stop 58 may be in the form of an iris diaphragm, or in the form of a releasably mounted baffle plate having a circular opening in the optical path. It is also noted that the stop 58 may be conjugate to the fundus of the normal eye, but it is desirable for the stop 58 to be axially movable in operative connection with a focusing control X of the focusing lens 43 so that the conjugation is adjusted in accordance with the visibility of the eye to be examined. A control mechanism is identified by the reference numeral 59.

An exciter filter 61 is movable to enter the illumination ray path of light (FIG. 21) and to retract therefrom (FIG. 22). A barrier filter 61 is movable to enter the photographic ray path of light and to retract therefrom. Both filters may be separately attached and detached, of course, but it is convenient to use an operative connection therebetween and to set the variator lens 43c to a short focal length (for small magnification) in response to insertion of the filters for fluorescein angiography and to a long focal length (for large magnification) in response to detachment of the filters (Y in FIG. 21). It is also convenient to open or detach the illumination field stop 58 in response to insertion of the filters for fluorescein angiography and to close down (FIG. 22) in response to detachment of the filters (FIG. 22). It is noted that in order to compensate for the change of length of the optical path resulting from the removal of the filters for fluorescein angiography there is another possible form in which an equivalent transparent plate substitutes for them.

With this type of camera, in fluorescein angiography, the exciter filter 60 and the barrier filter 61 are inserted into the respective optical paths, and the variator lens 43c is set in the short focal length position, thereby photographs can be taken in the same manner as in conventional eye fundus cameras.

In normal photography, the exciter filter 60 and the barrier filter 61 are retracted from the optical paths, and the variator lens 43c is moved to the long focal length position to increase the magnification of the photographic system, while the illumination field stop 58 is closed down. Upon adjustment of the position of the focusing lens 43a, in accordance with the visibility of the eye to be examined, the stop 58 is concurrently moved to focus the camera on the fundus of the eye and also to bring the stop 58 int conjugate with the eye fundus Ef. Here, the angle of projection of light from the energized light source 55 or 57 becomes equal to the photographic angular field of the photographic system. Also, even when the photographic angular field is narrowed, the disturbing reflections on the crystalline lens, if found to cause a loss in the image quality, will be eliminated by using a black point B conjugate to the fundus side surface of the crystalline lens in the optical path between the apertured mirror 42 and the light source, for example, the mirror 52 and the ring slit 53. But in fluorescein angiography, because it is unnecessary, the black point is either removed from the optical path or shifted axially to overlap the central light blocking portion of the ring slit 53. Thereby, the obscuring action is of no effect with the advantage that the level of illumination can be saved.

Figure 23:
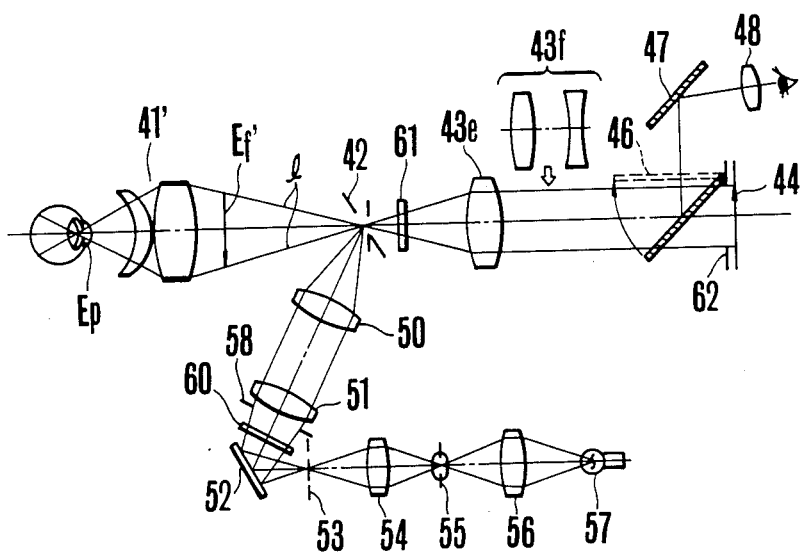
FIG. 23 is a sectional view of still another embodiment of the invention.

FIG. 23 illustrates an example of modification of the camera of FIGS. 21 and 22 where, instead of moving the variator lens 43c of FIG. 21, a telephoto type Bravais attachment lens 43f is attached or detached at the rear of the fixed lens 43e. When the attachment lens 43f is mounted in alignment with the optical axis, the magnification of the photographic system is increased with the establishment of a narrow angular field. It is noted that it is convenient to use an operative connection between the attachment lens and the illumination field stop 58.

On the other hand, if the area to be photographed becomes narrow compared to fluorescein angiography and if photographs of the same magnification are desired, it is better that, while the attachment lens 43f is left detached from the optical path, or the variator lens 43c is left unchanged from the short focal length position, the illumination field stop 58 is closed down. Furthermore, either the photographic field stop 62 is closed down to match the area to be photographed, or the film camera body is replaced by another interchangeable camera body having the required photographic field stop size.

According to the present invention, a fluorescein angiography of an extremely wide angle field becomes possible, and even in normal photography high contrast photographs can be obtained. Or, since the increase in image magnification permits converage of the same image formable area as when the magnification is low (wide angle), the film can be used without wasteful consumption. Particularly in enlarged prints from color photographs which are taken without a change of magnification, the loss in resolving power due to the grains of photosensitive material in the film can be advantageously reduced.

What is claimed is:

1. An eye fundus camera capable of selectively performing normal photography and fluorescein angiography comprising:
   (a) photographic means for forming a photographic optical path and for photographing the fundus of the eye, said photographic means having a conjugate field stop to the fundus of the eye to be examined;
   (b) illuminating means for forming an illuminating optical path and for illuminating the fundus of the eye, said illuminating means being provided with a conjugate ring slit to the front part of an eye to be examined with respect to an objective optical system confronting the eye;
   (c) light selecting means cooperating with said photographic means for selecting a light forming a fluorescein image from among the light from the eye fundus;
   (d) exciting means cooperating with said illuminating means for producing a light exciting fluorescein substance;
   (e) a second field stop arranged in said illuminating optical path approximately conjugate with the eye fundus of the eye to be examined for reducing the illuminated area of the eye fundus; and
   (f) means for making a diameter of the illuminated area of said second field stop smaller in connection with alteration from fluorescein angiography, with both said exciting means and said light selecting means in the optical path, to normal photography with both said exciting means and said light selecting means out of the optical path.

2. An eye fundus camera according to claim 1, further including:
   first operative connection means for causing insertion of at least one of said light selecting means and exciting stop into the optical path to occur with actuation of said limiting means.

3. An eye fundus camera according to claim 2, wherein said second field stop is an iris diaphragm.

4. An eye fundus camera according to claim 2, wherein said second field stop is an aperture.

5. An eye fundus camera according to claim 2, wherein said light selecting means is a barrier filter, and said exciting means is an exciter filter.

6. An eye fundus camera according to claim 1, wherein said field stop of said photographic means reducing the photographic field more in normal photography than in fluorescein angiography.

7. An eye fundus camera according to claim 6, wherein said field stop of said photographic means is an iris diaphragm.

8. An eye fundus camera according to claim 6, wherein said field stop of said photographic means is an aperture.

9. An eye fundus camera according to claim 6, wherein said field stop of said photographic means is provided in a camera body.

10. An eye fundus camera according to claim 1, wherein said photographic means has magnification varying means for increasing the magnification of said photographic means in the normal photography more than in the fluorescein angiography.

11. An eye fundus camera according to claim 1, wherein said photographic means having focusing means for focusing the photographic means on the fundus of an eye, and said eye fundus camera further including:
   shifting means for shifting said second field stop along the light path as focusing of said focus means is performed.

12. An eye fundus camera according to claim 1, wherein said illuminating means has baffling means for baffling undesirable light due to the crystalline lens of the eye to be examined in said illuminating light path, and wherein said camera further includes second operative connecting means for causing insertion of at least one of said light selecting means and said exciting means into the optical path to occur with movement of said baffling means.

13. An eye fundus camera according to claim 12, wherein said baffling means is moved away from said illuminating light path when in the fluorescein angiography.

14. An eye fundus camera capable of selectively performing normal photography and fluorescein angiography comprising:
   (a) photographic means for forming a photographic light path and photographing the fundus of an eye;
   (b) illuminating means for illuminating the fundus of the eye and forming an illuminating optical path;
   (c) light selecting means cooperating with said photographic means for selecting a light forming a fluorescein image from among the lights from the eye fundus;
   (d) exciting means cooperating with said illuminating means for producing a light exciting fluorescein substance;
   (e) a field stop arranged in said photographic optical path approximately conjugate with the eye fundus of the eye to be examined for reducing the imaging area of the eye fundus; and
   (f) means for making a diameter of said field stop smaller in connection with alteration from fluorescein angiography, with both said exciting means and said light selecting means in the light path, to normal photography with both said exciting means and said light selecting means out of the light path.

15. An eye fundus camera according to claim 14, further including:
   operative connection means for causing actuation of at least one of said light selecting means and said exciting means to occur along with release of said field stop from the positive action.

16. An eye fundus camera according to claim 14, wherein said field stop is an iris diaphragm.

17. An eye fundus camera according to claim 14, wherein said field stop is an apertured plate.

18. An eye fundus camera according to claim 14, further including:
   a second field stop arranged in said illuminating light path for more reducing that area of the eye fundus which is to be illuminated in the normal photography as compared in the fluorescein angiography and also to limit the eye fundus illuminating light.

19. An eye fundus camera according to claim 14, wherein said light selecting means is a barrier filter and said exciting means is an exciter filter.

20. An eye fundus camera according to claim 14, further including baffling means arranged in said illuminating light path upon normal photography for eliminating undesirable light due to the crystalline lens of the eye to be examined.

21. An eye fundus camera according to claim 18, further including baffling means arranged in said illuminating light path upon normal photography for eliminating undesirable light due to the crystalline lens of the eye to be examined.

22. An eye fundus camera capable of selectively performing normal photography and fluorescein angiography comprising:
   (a) photographic means for forming a photographic optical path and photographing the fundus of the eye, said photographic means including a field stop for making an eye fundus image forming area in a recording plane constant between in normal photography and in fluorescein angiography;
   (b) illuminating means for forming an illuminating optical path and illuminating the fundus of the eye;
   (c) exciting means cooperating with said illuminating means to provide a light exciting fluorescein substance;
   (d) light selecting means cooperating with said photographic means to select a light forming a fluorescein image from among the lights from the eye fundus; and
   (e) magnification varying means for reducing the magnification of said photographic means in connection with alteration from normal photography with both said exciting means and said light selecting means out of the optical path, to fluorescein angiography with both said exciting means and said light selecting means in the optical path, wherein both said photographic means and said illuminating means are constructed suitable for the photographing angle in fluorescein angiography which is wider than the photographing angle in normal photographing.

23. An eye fundus camera according to claim 22, further including:
   a second field stop arranged in said illuminating optical path for reducing an illuminated area on the fundus of the eye in normal photography compared with fluorescein angiography.

24. An eye fundus camera according to claim 23, wherein said a second field stop is an iris diaphragm.

25. An eye fundus camera according to claim 23, wherein said second field stop is an apertured plate.

26. An eye fundus camera according to claim 23, wherein said second field stop is arranged at a substantially optical conjugate point of position to the fundus of the normal eye.

27. An eye fundus camera according to claim 23, wherein said second field stop is movable along the illuminating optical path.

28. An eye fundus camera according to claim 22, wherein said magnification varying means has lens means movable along the optical axis of said photographic means.

29. An eye fundus camera according to claim 22, wherein said magnification varying means has lens means attachable to and detachable from the optical path of said photographic means.

30. An eye fundus camera according to claim 22, further including:
   operative connection means for causing reduction of the magnification by said magnification varying means to occur along with actuation by said light selecting means.

31. An eye fundus camera according to claim 22, further including:
   baffling means arranged in said illuminating light path for eliminating undesirable light due to the crystalline lens of the eye to be examined; and
   shifting means for shifting said baffling means in response to change in the magnification by said magnification varying means.

32. An eye fundus camera according to claim 23, further including baffling means arranged in said illuminating light path upon normal photography for eliminating undesirable light due to the crystalline lens of the eye to be examined.

33. A photographing process of an eye fundus camera capable of selectively making the normal photography and the fluorescein angiography, said camera including a barrier filter in the light path for eye fundus photography, an exciter filter in the light path for eye fundus illumination, and an optical system for eye fundus photography including a field stop for making an eye fundus image forming area on a recording plane constant between in normal photography and in fluorescein angiography, comprising the steps of:
   (a) detaching the barrier filter from the light path for eye fundus photography;
   (b) detaching the exciter filter from the light path for eye fundus illumination;
   (c) setting up the magnification of the optical system for eye fundus photography to a higher magnification side;
   (d) reducing the area of the eye fundus which is to be illuminated;
   (e) illuminating the eye fundus; and
   (f) exposing photographic film to the reflected light from the eye fundus; whereby the illuminating area is reduced and, at the same time, the magnification of the optical area is increased in connection with alteration from fluorescein angiography with both said exciter filter and said barrier filter in the light path, to normal photography with both said exciter filter and said barrier filter out of the light path.

34. A photographing process of the eye fundus camera according to claim 33, further including baffling means arranged in said illuminating light path upon normal photography for eliminating undesirable light due to the crystalline lens of the eye to be examined.

* * * * *